(12) United States Patent
Weng et al.

(10) Patent No.: US 10,786,326 B1
(45) Date of Patent: Sep. 29, 2020

(54) SURGICAL IMAGE PICKUP SYSTEM

(71) Applicant: NATIONAL APPLIED RESEARCH LABORATORIES, Taipei (TW)

(72) Inventors: Rui-Cian Weng, New Taipei (TW); Yih-Sharng Chen, Taipei (TW); Te-I Chang, New Taipei (TW); Chi-Hung Huang, Hsinchu (TW); Yen-Pei Lu, Hsinchu (TW); Yen-Song Chen, Taipei (TW); Kuan-Yin Yu, Taipei (TW)

(73) Assignee: National Applied Research Laboratories, Taipei (TW)

( * ) Notice: Subject to any disclaimer, the term of this patent is extended or adjusted under 35 U.S.C. 154(b) by 0 days.

(21) Appl. No.: 16/530,721

(22) Filed: Aug. 2, 2019

(30) Foreign Application Priority Data

Apr. 26, 2019 (TW) .............................. 108114802 A

(51) Int. Cl.
*A61B 90/00* (2016.01)
*H04N 5/225* (2006.01)
*G03B 13/36* (2006.01)
*G02B 25/00* (2006.01)
*H04N 7/18* (2006.01)

(52) U.S. Cl.
CPC .......... *A61B 90/361* (2016.02); *G02B 25/001* (2013.01); *G03B 13/36* (2013.01); *H04N 5/2254* (2013.01); *H04N 5/2256* (2013.01); *H04N 7/183* (2013.01); *A61B 2090/373* (2016.02)

(58) Field of Classification Search
CPC ............ A61B 90/361; A61B 2090/373; G02B 25/001; G03B 13/36; H04N 5/2254; H04N 5/2256; H04N 7/183
See application file for complete search history.

(56) References Cited

U.S. PATENT DOCUMENTS

| 2015/0297311 A1* | 10/2015 | Tesar | A61B 90/37 600/411 |
| 2016/0183779 A1* | 6/2016 | Ren | G02B 21/22 351/206 |
| 2016/0220324 A1* | 8/2016 | Tesar | A61B 90/25 |

* cited by examiner

*Primary Examiner* — Alexander Gee
(74) *Attorney, Agent, or Firm* — Muncy, Geissler, Olds & Lowe, P.C.

(57) ABSTRACT

A surgical image pickup system utilizes an adjustable lens set and a complex lens set to change the direction of the incident light emitted from the light source and the position of the surgical site on which the incident light projects. The eyepiece and the sensor have the same field of view and the same optical axis such that first image generated by the sensor and a second image generated by the eyepiece are the same. The sensor transmits the first image to the external display for display by wireless communication. By means of the foregoing configuration, the second image which doctor utilizes the eyepiece to see and the first image which the external display displays are the same, thereby facilitating the operation of surgery.

10 Claims, 4 Drawing Sheets

US 10,786,326 B1

SURGICAL IMAGE PICKUP SYSTEM

CROSS-REFERENCE TO RELATED APPLICATION

This application claims priority from Taiwan Patent Application No. 108114802, filed on Apr. 26, 2019 in Taiwan Intellectual Property Office, the disclosures of which are hereby incorporated by reference in their entirety for all purposes.

BACKGROUND OF THE INVENTION

1. Field of the Invention

The present invention relates to an image system, and particularly to a surgical image pickup system which utilizes same optical axis of the sensor and the eyepiece to obtain the same image.

2. Description of the Related Art

In modern surgical camera systems, a doctor wears a camera device, a projected light source, and an eyepiece, typically mounted on the head of the doctor, while an operator controls the position and the angle of view of the camera. When an image generated by the camera device is different from the image generated by the eyepiece, the doctor merely moves his head to adjust the projection angle and the position of the projected light source and the operator must adjust the camera device to find the surgical site because the camera device and the eyepiece do not have the same optical axis and the same field of view. Additionally, since the projection angle of the projected light source is limited, the luminance of the image generated by the camera device is not uniform. Hence, the modern surgical camera system creates inconvenience for the doctor and, as such, is a issue needing a solution.

Accordingly, the inventor of the present invention has designed a surgical image pickup system to overcome deficiencies in terms of current techniques so as to enhance the implementation and application in industries.

SUMMARY OF THE INVENTION

In view of the aforementioned known issues, the purpose of the present invention is to provide a surgical image pickup system to solve the problems found in the conventional techniques.

In order to achieve the objective, the present invention provides a surgical image pickup system. The surgical image pickup system comprises a sensor, an adjustable mechanism, a complex lens set and at least one eyepiece. The adjustable mechanism is configured adjacent to the sensor and comprises at least one adjustable lens set and at least one projected light source. The projected light source emits an incident light to an object under test, and the adjustable lens set is disposed on the optical axis of the projected light. The complex lens set is disposed between the sensor and the object under test and focuses the incident light to project on the object under test. Each eyepiece is configured adjacent to the complex lens set. Wherein, the sensor and the eyepiece respectively receives a reflection light reflected from the incident light projected on the object under test and respectively forms a first image and a second image. The complex lens set and the adjustable lens set respectively adjust the travelling direction of the incident light and the position on which the incident light projects. The sensor and the eyepiece are respectively provided with an identical field of view. Hereby, the first image is the same as the second image. By using the foregoing configuration, the first image generated by the sensor is the same as the second image generated by the eyepiece and it facilitates convenience for the doctor to perform the surgery.

Preferably, the sensor and the eyepiece have a same optical axis.

Preferably, the plane where the projected light source is located is orthogonal to the plane where the complex lens set is located.

Preferably, the distance between the eyepiece and the object under test is less than the distance between the sensor and the object under test.

Preferably, the surgical image pickup system further comprises at least one marking element, the marking element is disposed in the adjustable mechanism to mark a sign on the object under test.

Preferably, the sensor is included in a camera device, the camera device further comprises a transmitter connected to the sensor, the transmitter transmits the first image of the sensor to an external display and the external display shows the first image.

Preferably, the camera device further comprises an auto-focus element and the auto-focus element adjusts a focus of the camera device.

Preferably, each of the adjustable lens set constitutes a plurality of reflective mirrors to change the travelling direction of the incident light, and there is an angle founed between the plane where each reflective mirror is located and the plane perpendicular to the sensor.

Preferably, the adjustable mechanism comprises a plurality units of the adjustable lens set and a plurality units of the projected light sources, and the plurality of adjustable lens set and the plurality of projected light sources are configured to surround the sensor.

Preferably, the number of the eyepieces is at least two and the eyepieces are symmetrically disposed to each other.

According to above contents, the surgical image pickup system of the present invention utilizes the same field of view and the same optical axis of the sensor and the eyepiece to make the first image of the sensor same as the second image of the eyepiece. Hence, it facilitates the doctor with convenience to perform the surgery. Besides, the external display receives and shows the first image so that the doctor is able to see the first image and the surgical site clearly.

DESCRIPTION OF THE PREFERRED EMBODIMENTS

Figure 1:
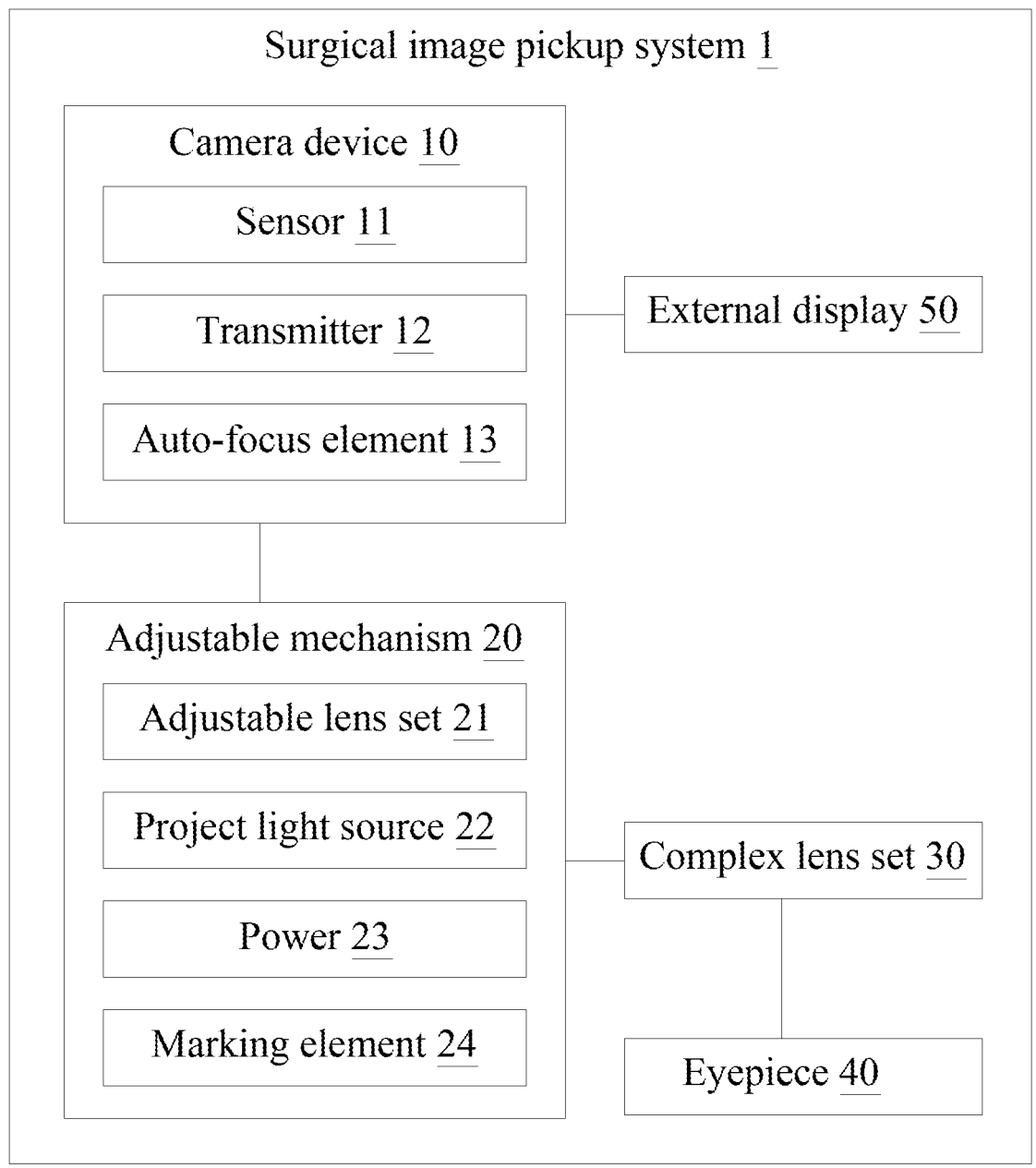
FIG. 1 depicts a block diagram of the surgical image pickup system according to the present invention.

The following embodiments of the present invention are herein described in detail with reference to the accompanying drawings. These drawings show specific examples of the embodiments of the present invention. It is to be acknowledged that these embodiments are exemplary implementations and are not to be construed as limiting the scope of the present invention in any way. Further modifications to the disclosed embodiments, as well as other embodiments, are also included within the scope of the appended claims. These embodiments are provided so that this disclosure is thorough and complete, and fully conveys the inventive concept to those skilled in the art. Regarding the drawings, the relative proportions and ratios of elements in the drawings may be exaggerated or diminished in size for the sake of clarity and convenience. Such arbitrary proportions are only illustrative and not limiting in any way. The same reference numbers are used in the drawings and description to refer to the same or like parts.

It is to be acknowledged that, although the terms 'first', 'second', 'third', and so on, may be used herein to describe various elements, these elements should not be limited by these terms. These terms is are used only for the purpose of distinguishing one component from another component. Thus, a first element discussed herein could be termed a second element without altering the description of the present disclosure. As used herein, the term "or" includes any and all combinations of one or more of the associated listed items.

It will be acknowledged that when an element or layer is referred to as being "on," "connected to" or "coupled to" another element or layer, it can be directly on, connected or coupled to the other element or layer, or intervening elements or layers may be present. In contrast, when an element is referred to as being "directly on," "directly connected to" or "directly coupled to" another element or layer, there are no intervening elements or layers present.

In addition, unless explicitly described to the contrary, the word "comprise" and variations such as "comprises" or "comprising", will be acknowledged to imply the inclusion of stated elements but not the exclusion of any other elements.

Figure 2:
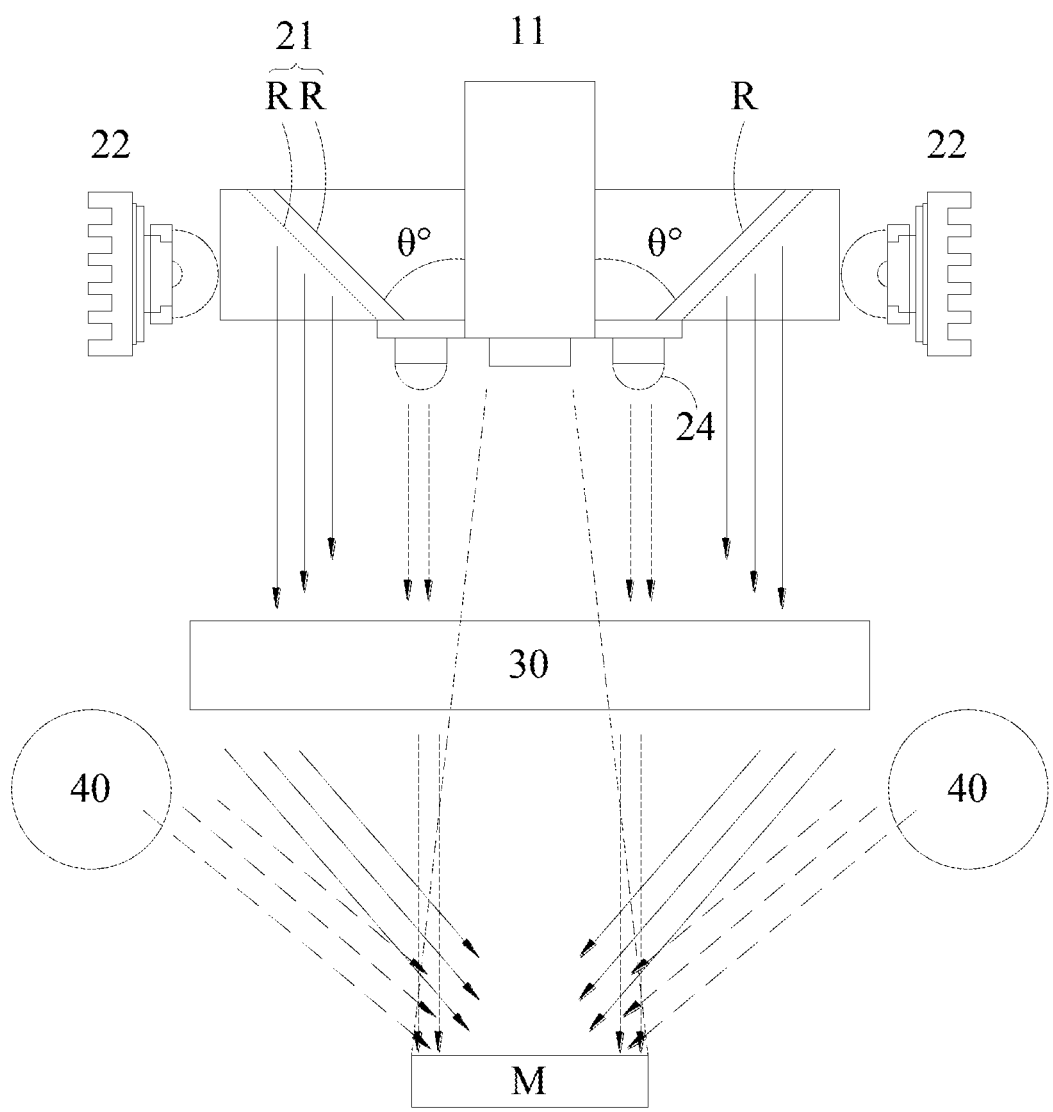
FIG. 2 depicts a configuration diagram of the surgical image pickup system according to the present invention.
Figure 3:
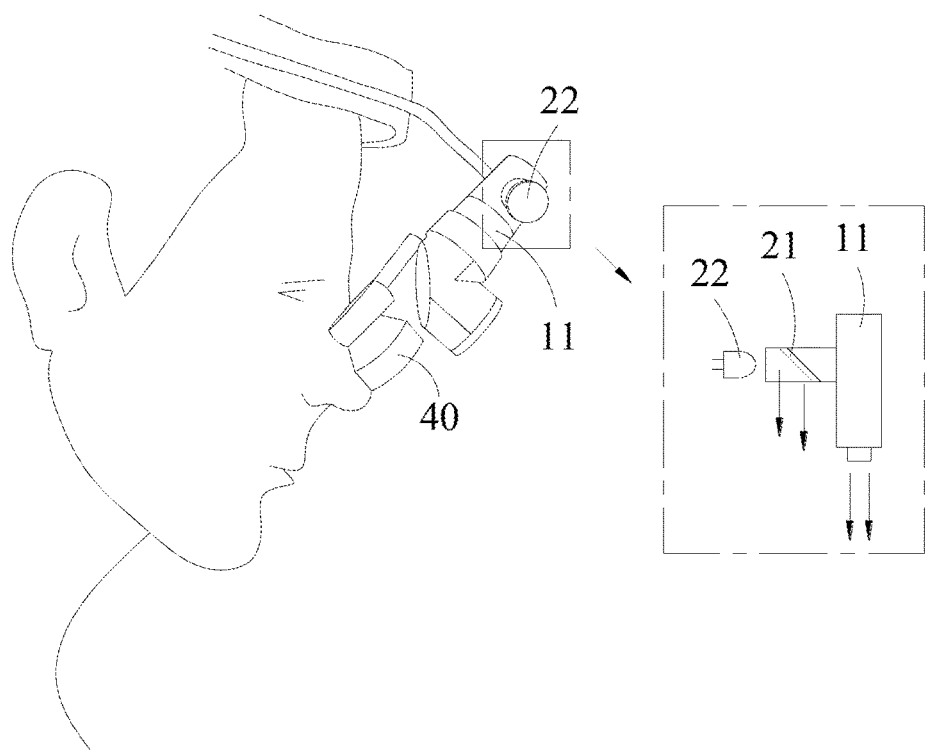
FIG. 3 depicts a using schematic view of the surgical image pickup system according to the present invention.

Please refer to FIG. 1, FIG. 2 and FIG. 3, which depict a block diagram of the surgical image pickup system according to the present invention, a configuration diagram of the surgical image pickup system according to the present invention and a using schematic view of the surgical image pickup system according to the present invention. As illustrated by FIG. 1, FIG. 2 and FIG. 3, the surgical image pickup system 1 of the present invention comprises a camera device 10, an adjustable mechanism 20, a complex set 30, two eyepieces 40 and an external display 50. In detail, the adjustable mechanism 20 comprises two adjustable lens sets 21, two projected light sources 22, a power 23 and two marking elements 24. Each projected light source 22 emits an incident light to an object under test M, and each adjustable lens set 21 is disposed on the optical axis of the corresponding projected light source 22 to turn the incident light to the object under test M. Each marking element 24 marks a sign on the object under test M. The power 23 provides the electrical energy to each projected light source 22. The projected light sources 22 and marking elements 24 may comprise light-emitting diode or laser diode. The projected light sources 22 and marking elements 24 may comprise the other preferable light source, and the scope of the present invention is not limited to above example. The camera device 10 comprises a sensor 11, a transmitter 12 and an auto-focus element 13. The sensor 11 is electrically connected to the transmitter 12, and the sensor 11 and two eyepieces 40 have a same optical axis. The sensor 11 is configured adjacent to the complex set 30. The adjustable mechanism 20 is configured adjacent to the sensor 11. The auto-focus element 13 adjusts the focus of the camera device 10. The complex set 30 is disposed between the sensor 11 and the object under test M and the complex set 30 focuses the incident light on the object under test M. The plane where each projected light source 22 is located is orthogonal to the plane where the complex lens set 30 is located. The eyepiece 40 is configured adjacent to the complex lens set 30 and the distance between the eyepiece 40 and the object under test M is less than the distance between the sensor 11 and the object under test M.

Here, the description how to form the first image and the second image by the sensor 11 and the eyepiece 40 is depicted as follows: When each projected light source 22 respectively emits the incident light to the corresponding adjustable lens set 21, each adjustable lens set 21 turns the incident light to the complex lens set 30. The complex lens set 30 focuses the incident light on the object under test NI. The object under test M reflects the incident light to the sensor 11 and each eyepiece 40. The sensor 11 and each eyepiece 40 respectively generate the first image and the second image. Each marking element 24 marks a sign on the object under test NI and the first image and the second image all have a sign. As the sensor 11 and the eyepiece 40 have the same optical axis and the complex lens set 30 and the adjustable lens sets 21 adjust the travelling direction of the incident light and the position of the object under test M where the incident light projects, the first image is the same as the second image. In other words, the image range of the sensor 11 and the eyepiece 40 viewed from the object under test M are the same as the projection range of the projected light sources 22 and it is convenient for the doctor to adjust the surgical site of the sensor 11 and the eyepieces 40.

The transmitter 12 then transmits the first image to the external display 50 to display, and the second image generated by the eyepieces 40 is the same as the first image showed by the external display 50. Hence, it facilitates the doctor with convenience to perform the surgery. Since the external display 50 has been provided with the memory and the image processor, the image processor performs image processing on the first image, and the first image showed by the external display 50 is clear and beneficial for the doctor to see.

It is worthy to mention that each of the adjustable lens set 21 constitutes a plurality of reflective mirrors R and there is an angle θ formed between the plane where each reflective mirror R is located and the plane perpendicular to the sensor 11. That is, each reflective mirror is obliquely set to reflect the incident light to the complex lens set 30. The number of the reflective mirrors R may be two or three as example and may be adjusted according to the actual conditions, and the scope of the present invention is not limited to above example. Each of the adjustable lens set 21 may be a reflective crystal to reflect the incident light to the complex lens set 30. Each of the adjustable lens set may be other preferable light elements that turn the incident light and the scope of the present invention which are not limited to the above example. The adjustable mechanism 20 may comprises a plurality units of the adjustable lens sets 21 and a plurality units of the projected light sources 22. The number of the eyepieces 40 is at least two. The present invention is not limited to two adjustable lens sets 21, two projected light sources 22 and two projected light sources 22. The plurality of adjustable lens sets 21 and the plurality of projected light sources 22 are configured to surround the sensor 11 with reference to the sensor 11. Many eyepieces 40 are disposed on two sides of the sensor 11 with reference to the sensor 11. The number of adjustable lens sets 21 and projected light sources 22 may be adjusted according to the actual situation and the scope of the present invention is not limited to above example.

Figure 4:
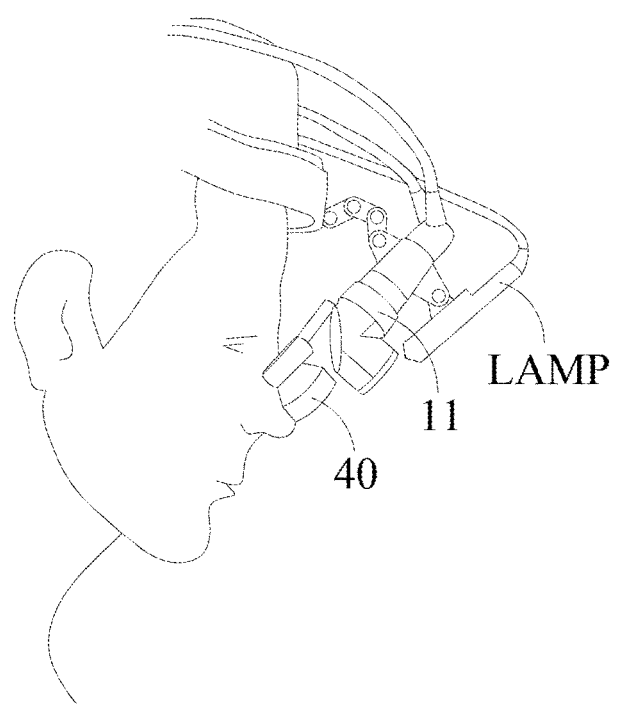
FIG. 4 depicts a using schematic view of the conventional surgical camera system.

Please refer to FIG. 4, depicts a using schematic view of the conventional surgical camera system. As illustrated by FIG. 4 and in comparison with FIG. 3, in the conventional surgical camera system, the halogen lamp LAMP is in front of the sensor 11 and the halogen lamp LAMP, the sensor 11 and the eyepieces 40 does not have the same optical axis. The images formed by the sensor 11 and the eyepieces 40 are different from each other. Differently, in the surgical image pickup system of the present invention, the projected light source 22 is on the one side of the sensor 11 with reference to the sensor 11 and the light emitted from the projected light source 22 is incident on the object under test M by the adjustable lens sets 21. Hence, the received light of the sensor reflected from the object under test NI and the light from the projected light source 22 after adjusted by the adjustable lens sets 21 are parallel with each other. The projected light source 22, the sensor 11 and the eyepiece 40 have the same optical axis. The image generated by the sensor 11 and the eyepiece 40 are the same and it is beneficial for doctor to perform the surgery.

Figure 5:
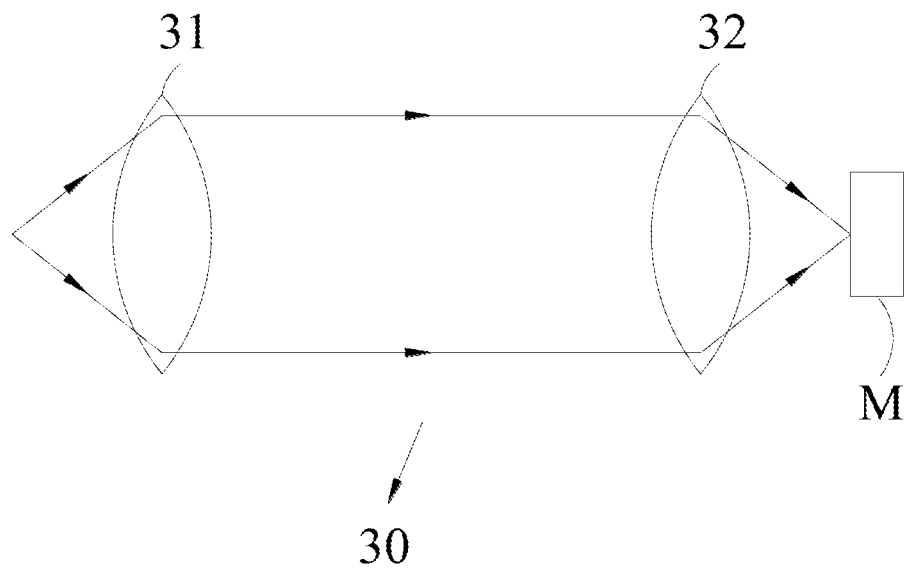
FIG. 5 depicts a configuration diagram of the complex lens set of the first embodiment of the surgical image pickup system according to the present invention.

Please refer to FIG. 5, which depicts a configuration diagram of the complex lens set of the first embodiment of the surgical image pickup system according to the present invention. As illustrated by FIG. 5, the complex lens set 30 comprises a first convex mirror 31 and a second convex mirror 32. The first convex mirror 31 expands the incident light reflected from the adjustable lens sets 21. The second convex mirror 32 focuses the expanded incident light on the object under test M, thereby focusing the incident light reflected from the adjustable lens sets 21 on the object under test M. This configuration make the incident light reflected from the adjustable lens sets 21 project on the object under test NI totally, thereby reducing the optical loss.

Figure 6:
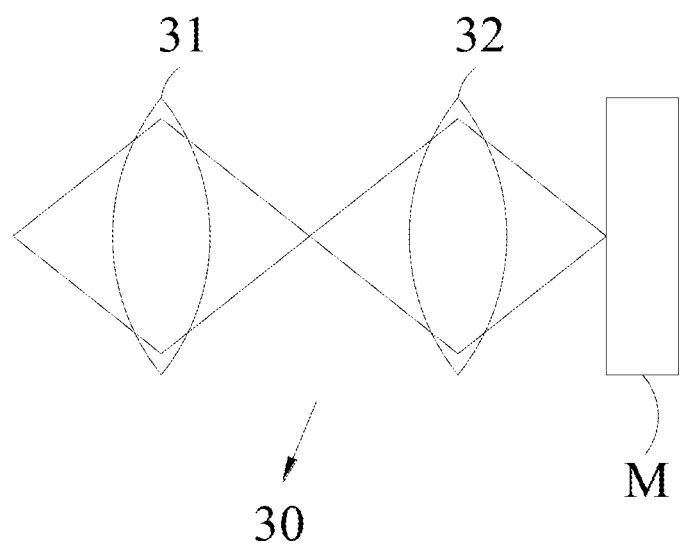
FIG. 6 depicts a configuration diagram of the complex lens set of the second embodiment of the surgical image pickup system according to the present invention.

Please refer to FIG. 6, which depicts a configuration diagram of the complex lens set of the second embodiment of the surgical image pickup system according to the present invention. As illustrated by FIG. 6, the complex lens set 30 comprises the first convex mirror 31 and the second convex mirror 32. The first convex mirror 31 focuses the incident light reflected from the adjustable lens sets 21 on the focus point of the first convex mirror 31. The focus point of the first convex mirror 31 is the same as the focus point of the second convex mirror 32. The second convex mirror 32 focuses the incident light passing through the first convex mirror 31 on the object under test M, thereby focusing the incident light reflected from the adjustable lens sets 21 on the object under test M. The advantage of this configuration is that the optical path of the second embodiment is shorter and it shortens the size of the surgical image pickup system.

The foregoing configurations of the complex lens set 30 are examples. The complex lens set 30 may be the other preferable configuration and the scope of the present invention is not limited to above example. The first convex mirror 31 and the second convex minor 32 may be spherical mirrors or aspherical mirrors. The first convex mirror 31 and the second convex mirror 32 are better as the aspherical mirrors to improve the spherical aberration and the coma aberration.

According to above-mentioned contents, the surgical image pickup system 1 of the present invention utilizes the same field of view and the same optical axis of the sensor 11 and the eyepiece 40 to make the first image of the sensor same as the second image of the eyepiece. Hence, it facilitates the doctor to perform the surgery. The external display 50 receives and shows the first image so that the doctor is able to see the first image and the surgical site clearly. In summary, the surgical image pickup system of the present invention has the above advantages and is beneficial for the doctor to perform surgery.

The present invention may be realized in different forms and should not be construed as being limited to the embodiments mentioned herein. It is to be understood that many other possible modifications and variations can be made by persons having ordinary skill in the art without departing from the spirit and scope of the invention as hereinafter claimed.

What is claimed is:

1. A surgical image pickup system comprising:
   a sensor;
   an adjustable mechanism, configured adjacent to the sensor and comprising at least one adjustable lens set and at least one projected light source, the projected light source emitting an incident light to an object under test, and the at least one adjustable lens set disposed on an optical axis of the projected light source;
   a complex lens set, disposed between the sensor and the object under test and focusing the incident light to be projected on the object under test; and
   at least one eyepiece, configured adjacent to the complex lens set;
   wherein the sensor and the eyepiece respectively receive a reflection light reflected from the incident light projected onto the object under test and respectively to form a first image and a second image, the complex lens set and the at least one adjustable lens set respectively adjust a travelling direction of the incident light and a position on which the incident light is projected, the sensor and the eyepiece respectively are provided with a same field of view and the first image is the same as the second image.

2. The surgical image pickup system of claim 1, wherein the sensor and the eyepiece have a same optical axis.

3. The surgical image pickup system of claim 1, wherein the plane where the projected light source is located is orthogonal to the plane where the complex lens set is located.

4. The surgical image pickup system of claim 1, wherein a distance between the eyepiece and the object under test is less than a distance between the sensor and the object under test.

5. The surgical image pickup system of claim 1, further comprising at least one marking element, wherein the marking element is disposed in the adjustable mechanism to mark a sign on the object under test.

6. The surgical image pickup system of claim 1, wherein the sensor is included in a camera device, the camera device further comprises a transmitter connected to the sensor, the transmitter transmits the first image of the sensor to an external display and the external display shows the first image.

7. The surgical image pickup system of claim 6, wherein the camera device further comprises an auto-focus element and the auto-focus element adjusts a focus of the camera device.

8. The surgical image pickup system of claim 1, wherein each of the at least one adjustable lens set constitutes a plurality of reflective mirrors to change the travelling direction of the incident light, and there is an angle formed between the plane where each of the plurality of reflective mirrors is located and the plane perpendicular to the sensor.

9. The surgical image pickup system of claim 1, wherein the adjustable mechanism comprises the plurality of adjustable lens sets and the plurality of projected light sources, and the plurality of adjustable lens sets and the plurality of projected light sources are configured to surround the sensor.

10. The surgical image pickup system of claim 9, wherein a number of the eyepieces is at least two and the eyepieces are symmetrically disposed to each other.

* * * * *